United States Patent [19]
Dorin et al.

[11] Patent Number: 5,985,037
[45] Date of Patent: Nov. 16, 1999

[54] PERCOLL AND SUGAR SELF-FORMING DENSITY GRADIENT

[75] Inventors: Melvin Dorin, Mountain View; Paul J. Voelker, Fremont, both of Calif.

[73] Assignee: Beckman Coulter, Inc., Fullerton, Calif.

[21] Appl. No.: 09/065,664

[22] Filed: Apr. 23, 1998

[51] Int. Cl.$^6$ ............................... C13F 3/00; G01N 9/30; B04B 15/10

[52] U.S. Cl. ............................... 127/29; 422/72; 422/101; 494/27

[58] Field of Search ............................... 127/29; 422/72, 422/101; 494/27

[56] References Cited

U.S. PATENT DOCUMENTS 4,480,038  10/1984  Cheng ........................................ 435/261
5,171,539  12/1992  Coombs ...................................... 422/101

OTHER PUBLICATIONS

CA 101:187340, Nagy et al, "Rapid Preparation of . . . ", 1984.

CA 107:130325, Symons et al, "Isolation of highly purified . . . ", 1987.

CA 106:47644, Jadot et al, "Intracellular pathway followed by . . . ", 1986.

*Primary Examiner*—David Brunsman
*Attorney, Agent, or Firm*—William H. May; P. R. Harder; Thomas Schneck

[57] ABSTRACT

A stable self-forming density gradient is created by applying a centrifugal field to a solution that contains 27–33% Percoll (v/v) and 36–44% sugar (w/w). This density gradient is stable for several hours, allowing separation of low sedimentation particles, such as subcellular particles.

15 Claims, 5 Drawing Sheets

PERCOLL AND SUGAR SELF-FORMING DENSITY GRADIENT

FIELD OF THE INVENTION

This invention relates to density gradients for separation or isolation of compounds based on the compound's density. Specifically, the invention relates to a self-forming density gradient.

BACKGROUND OF THE INVENTION

A common and useful technique in the biological and physical sciences involves separation or isolation of compounds of discrete density by density fractionation. One method to effect this separation is density gradient centrifugation. In the biological sciences, variations in cell types, differences in the phenotype of cellular components, variation in DNA base or isotope composition, and isolation of the viral genomes and proteins have all been effected by density gradient centrifugation. To effect this technique, a solution of continuously varying concentrations is contained within a centrifuge tube. The solution will be most concentrated at the bottom of the tube and least concentrated at the top. A sample to be analyzed is then introduced into the tube. Next, a centrifugal field is applied to the tube at the top. As the centrifugal force is applied, the compounds within the tube will migrate toward the outer radius (i.e. tube bottom for swinging bucket rotors, tube side for vertical tube rotors) based on density and separate into isopycnic bands at discrete levels within the centrifuge tube. These bands can then be recovered from the tube, further purified if necessary, and analyzed.

To effect a density gradient centrifugal separation, a density gradient must be formed. This requires layering solutions of lighter density on top of solutions of heavier density. Solutions of sucrose of decreasing concentrations can be layered one on top of another to form a linear gradient from, for example 10–40% from the top of the tube to the bottom. In a linear gradient, the density varies equally along the length of the tube. The solutions of higher density are more viscous. Thus, a density gradient establishes a viscosity gradient in the tube as well. Ordinarily, for swinging bucket rotors, the g forces are greatest at the bottom of the tube which has a greater radius from the center of rotation than the top of the tube. The viscosity gradient counteracts the g force difference, allowing a nearly uniform migration rate of particles throughout the tube. The gradient also prevents mixing of the contents of the tube during acceleration and deceleration. This allows the formation of discrete isopycnic bands.

Several techniques have been developed to form linear density gradients. A first technique involves having a sucrose solution at a uniform concentration undergo repeated cycles of freezing and thawing. This freeze-thaw technique produces a gradient because the ice floats, excluding the sugar. However, this method has several drawbacks. The technique has poor reproducibility due to variations in the freeze-thaw cycles and is time intensive. Furthermore, any other compounds in solution in addition to the sugar would also be excluded from forming ice crystals, resulting in changes to the buffer concentration throughout the tube. This could affect the stability of a sample the researcher is seeking to separate.

A second technique of forming sucrose density gradients entails simply layering various concentrations of sucrose by hand. In this technique, a plurality of sucrose solutions are each layered into a centrifuge tube. The solution with the lowest concentration would be added first to the tube, with subsequent layers added by pipette from the bottom of the tube, causing flotation of previously inserted layers. This method will not result in a complete gradient, but instead will be stepwise concentration changes. This method is a laborious process with low reproducibility.

In U.S. Pat. No. 5,171,539, the process of gradient formation is automated to allow greater reproducibility. This patent describes an apparatus for holding centrifuge tubes and moving the tubes into a programmed orientation. By including a low concentration sucrose solution floated over a high concentration sucrose solution, the rotation of the tube would produce a mechanically reproducible gradient. The patent notes at col. 5, lines 46–49, that if sucrose is not used to make the gradient, the gradient could alternatively be formed by using Percoll. This technique, although improving the reproducibility, requires purchase of additional gradient forming apparatus and required time for the apparatus to form the density gradient.

Some ability to produce self-forming gradients is known. For example, U.S. Pat. No. 4,480,038 describes using a 60% Percoll gradient to separate cells. A very small quantity of the sugar sucrose is added for osmolarity. Under a relative short spin time (45 min.) under a centrifugal field of 100,000×g density markers would separate. However, many experimental protocols for separating compounds with low migration rates would require density gradients that are stable for spin times of several hours. For example, subcellular particles, unlike the cells described in U.S. Pat. No. 4,480,038, have low sedimentation rates. If a more stable self-forming density gradient could be developed, it would greatly simplify and improve density gradient separations that require longer spin times.

It is the object of this invention to provide a process for producing a self-forming density gradient. Because this gradient would be self-forming, producing the gradient would be rather simple and would take minimal time. Additionally, a self-forming gradient would not require the purchasing of additional instrumentation since the gradient would automatically form in a centrifugal field.

Another object of the invention is to devise a method for enhancing the reproducibility of gradient formation.

Another object of the invention is to devise a density gradient that can be used in high capacity rotors allowing for greater experimental throughput.

Finally, the invention should require only inexpensive materials, be easy to prepare, easy to use, and adaptable to a variety of experimental protocols.

SUMMARY OF THE INVENTION

The objects of the invention are achieved by combining known compounds to produce a new method of forming a density gradient. This gradient is self-forming, requiring nothing more than applying a centrifugal force to form the gradient. In the present invention, a density gradient is formed by adding 27–33% Percoll (v/v) to a centrifuge tube and dissolving into this 36–44% sugar (W/W) into said tube, and applying the centrifugal force until a linear gradient has formed. In the preferred embodiment, 30% (v/v) Percoll is added to 40% (w/w) sorbitol and mixed until the sorbitol is dissolved. The centrifugal force is applied by spinning the centrifuge tube for 3 hours at 50,000 RPM at 5 degrees C. in a vertical tube centrifuge rotor with a sample radius maximum at 86.6 mm. This results in 242,500×g in force. In the preferred embodiment, this is effected in a vertical tube rotor. By using a vertical tube rotor, the path-length any given sample or particle must travel is minimized. Further, the short path-length also allows for an efficient establishment of the density gradient.

Another aspect of the invention is the density gradient itself. This density gradient is comprised of 27–33% (v/v) solution of sterile Percoll and 36–44% (w/w) sugar. In the preferred embodiment, the sugar is sorbitol at 40% concentration. However, sucrose and other sugars may be used. In the preferred embodiment, the Percoll is at 30% (v/v) concentration.

BEST MODE FOR CARRYING OUT THE INVENTION

For purposes of the present invention, the following terms are described.

"Percoll" is the registered trademark of Pharmacia, Sweden. Percoll is a colloidal silica sol with nondialysable polyvinyl pyrrolidone (pvp) coating. Percoll is sold in solution in water under code no. 17-0891-01.

"Sugar" refers to any monosachride or disachride. These compounds have densities in the 1.475–1.600 range and molecular weights in the 160–360 range.

Previously, Percoll was known to produce a self-forming gradient in a centrifugal field. However, such gradients would rapidly degrade as the Percoll would migrate to the bottom of the centrifuge tube, forming a pellet. This would allow for the Percoll density gradient separations that required short spin times for compounds or cells with high sedimentation rates. However, separations of viral particles, intercellular organelles, or intercellular parasitic organisms require longer spin times due to a lower sedimentation rate for these associated particles and compounds. Previously, it has not been realized that Percoll in specific concentrations when combined with a sugar such as sorbitol or sucrose in a specific concentration could yield a self-forming density gradient suitable for the separation of low sedimentation particles, such as subcellular particles.

Figure 1:
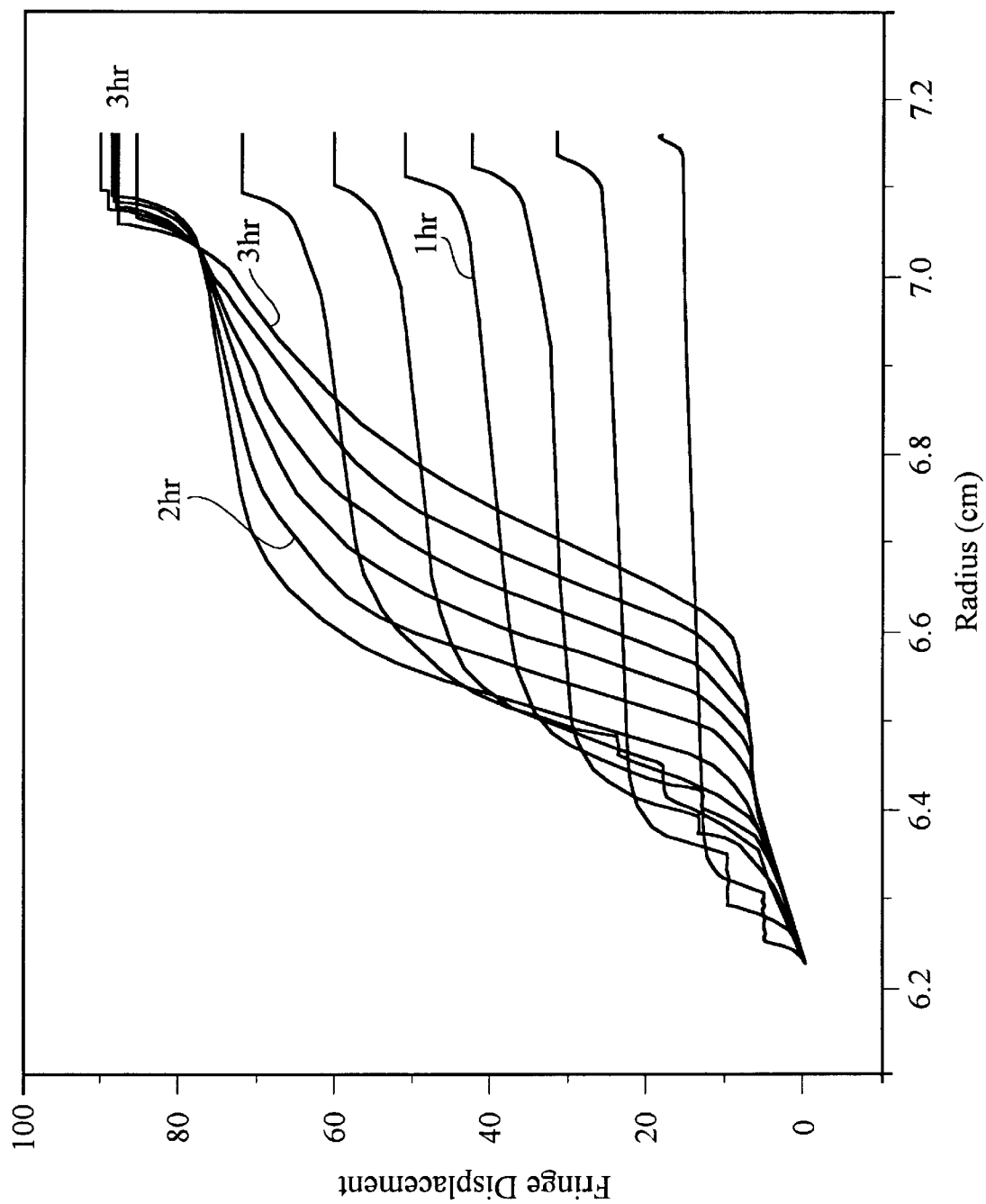
FIG. 1 is a plot of a time course gradient formation using a ratio of 100% Percoll and 75% sucrose.
Figure 2:
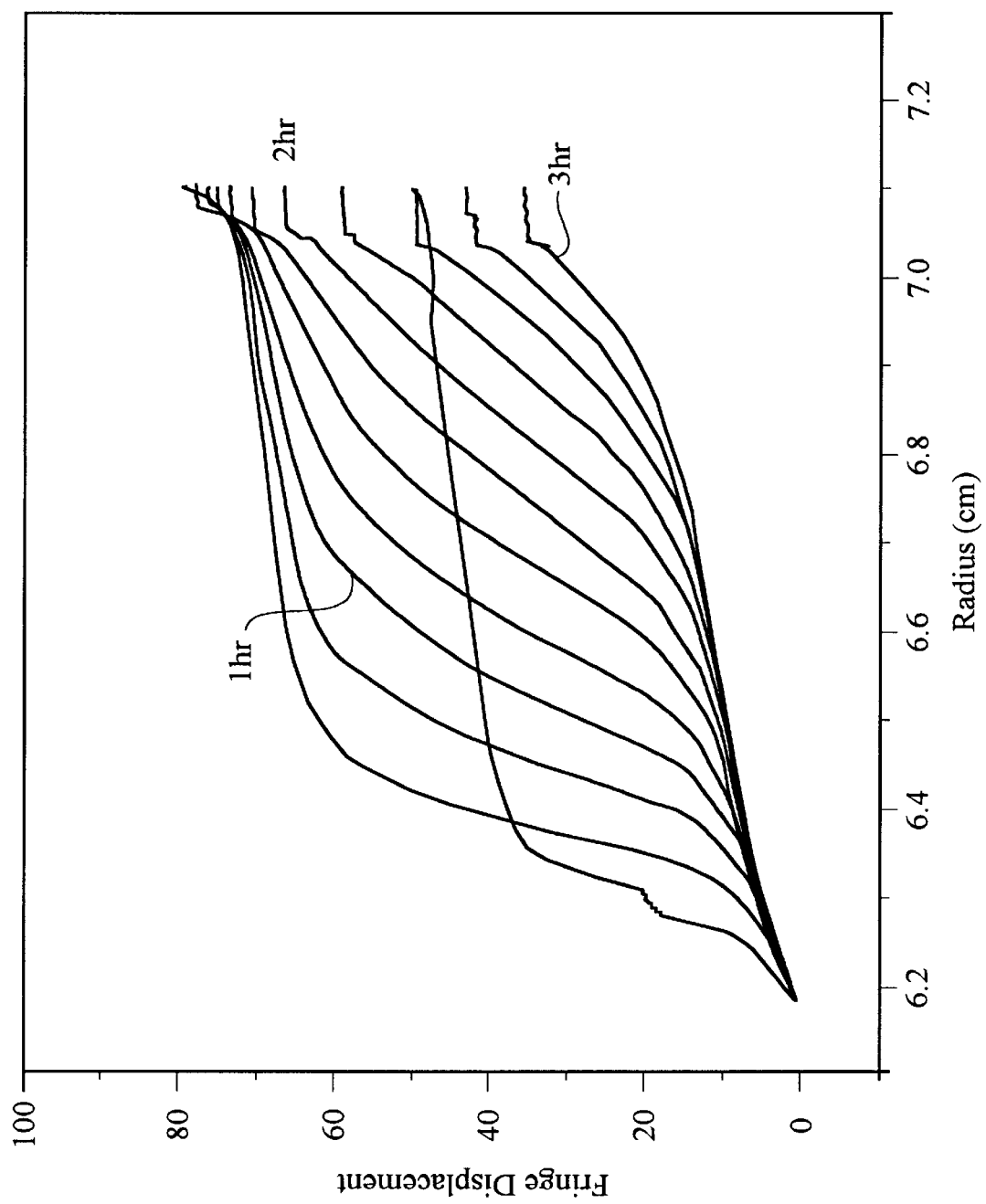
FIG. 2 is a plot of a time course gradient formation using a ratio of 75% Percoll and 40% sucrose.
Figure 3:
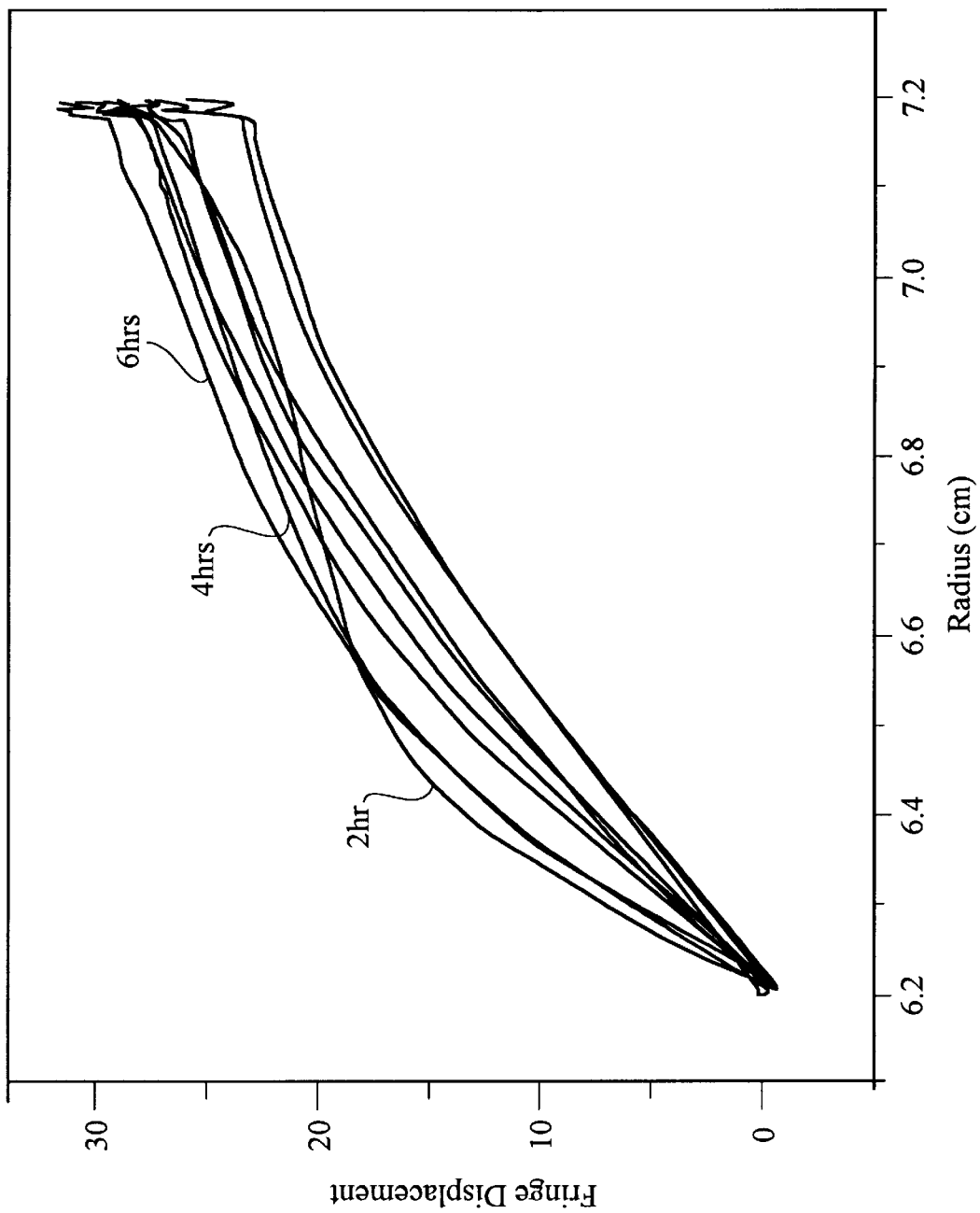
FIG. 3 is a plot of a time course gradient formation using a ratio of 30% Percoll and 30% sucrose.

FIGS. 1, 2, and 3 show the variation of stability of gradients when the amount of Percoll and sucrose are varied. Results were collected on an analytical ultracentrifuge equipped with interference optics which measures the total concentration of material present as a function of refraction. The 6.2 to 7.0 radius (the x-axis) represents the path length of the centrifuge tube. The total concentration is depicted graphically (the y-axis) as fringe displacement and is correlated with density. The ideal gradient would form smoothly over the course of a run and cover a fixed density range. These runs were performed in a Beckman AN-60Ti rotor and spun at 35,000 rpms (98,784×g resulting g force). These runs were performed at 20 degrees C.

FIG. 1 shows the fringe displacement of a solution of 100% Percoll (v/v) and 40% sucrose (W/W) after 1,2,3 hours. The gradient profile after one hour is rather shallow. Almost the entire change in density within the tube occurs at a very small radial fraction at 6.4 cm. After 2 and 3 hours, the tubes exhibit a rather steep gradient change, with fringe displacement at 80%. At 2 and 3 hours, as was seen at 1 hour, the density change was concentrated at a small radial fraction within the tube, in this case at 6.5 and 6.6 respectively. Thus, these ratios of Percoll and sucrose do not establish a linear density gradient.

FIG. 2 shows the fringe displacement of a solution of 75% Percoll (v/v) and 40% sucrose (W/W) after 1,2,3 hours. Again when viewed over time, the structure of the density gradient changes dramatically. Thus, the time of ending the centrifuge density separation would determine where the sample particles would be located. Since the density gradient is so steep for much of the separation run, particles would forms bands only within a narrow radial length within each tube. This is suboptimal for separation of particles with similar densities, for instance separation of satellite DNA or viral particles. The density profile after one hour shows a steep rise at a narrow radial section located at 6.5 cm. Similarly, after 2 hours, the gradient is rather steep, the density change is concentrated in the radial section from 6.7 to 6.9 cm. By the third hour, the gradient has collapsed. In both FIGS. 1 and 2, the profile of the gradient shows dramatic temporal variance. The location of the sample, or even the ability to separate compounds of varied density at all, would change throughout the spin run time.

In contrast, FIG. 3 depicts the results achieved with the present invention. The results are rather different. The gradient profiles, shown at two, four and six hours are substantially similar. The gradient also show near linear variation across the entire tube length. This is the near ideal gradient formation for separation of low sedimentation rate particles. The particles would exhibit nearly identical migration rates throughout the centrifuge run because the particles would be subject to nearly constant force throughout the run. Because the density gradient profile is nearly uniform, slight changes in the run end time would have less effect on the final location of a sample to be separated.

Figure 4:
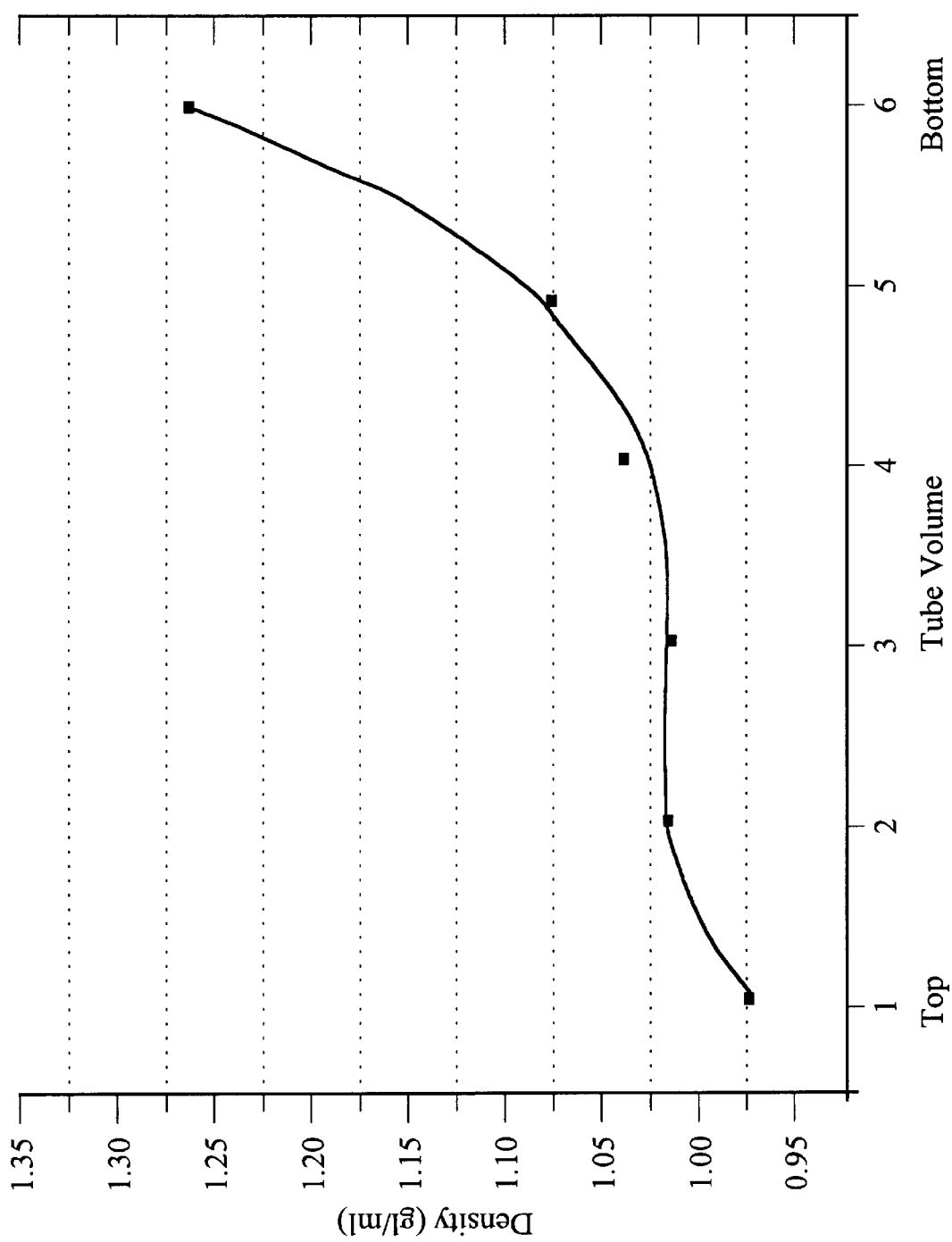
FIG. 4 is a plot of a gradient formation in eight minutes using only a 30% solution of Percoll.

FIG. 4 shows the density profile of a 30% Percoll solution spun in a Beckman VTi 50 rotor at 30,000 RPM for 8 min. The run was performed in a 39 ml tube at 20 degrees C. The density profile shows the beginning of a density gradient collapse. The density variation is concentrated at the bottom third of the tube, where the density gradient is rather steep. Within a few minutes later, the density profile would not exist, as the Percoll would have formed a pellet at the bottom of the tube.

Figure 5:
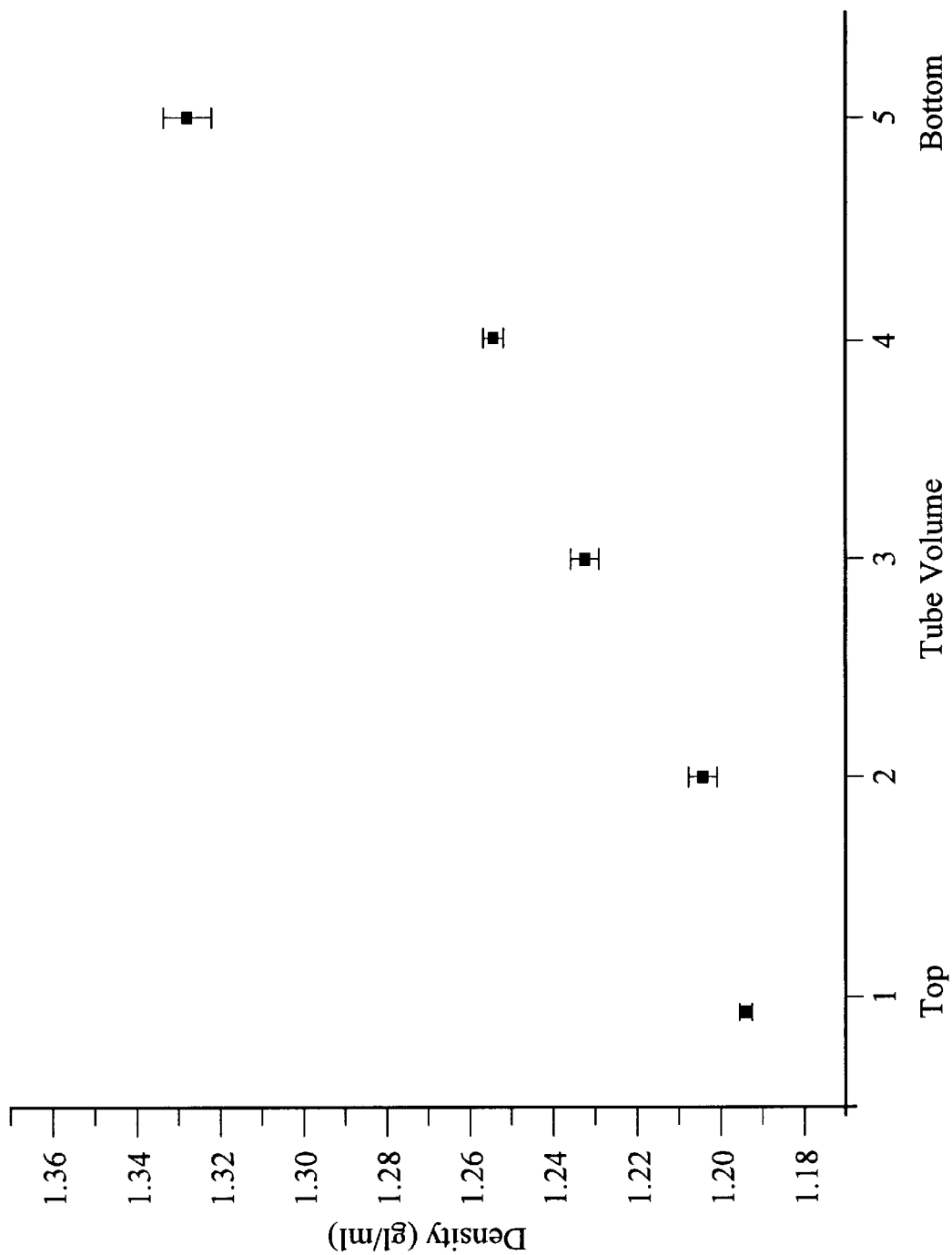
FIG. 5 is a plot of the density gradient formation using the preferred concentrations: 30% Percoll and 40% sorbitol.

In contrast, FIG. 5 shows the density profile of the ideal formulation, 30% Percoll (v/v) and 40% sorbitol (W/W). This separation was also performed in a 39 ml quick seal tube using a Beckman VTi 50 rotor. The sample was spun for three hours at 50,000 RPM. The graph shows that even after spinning for three hours, the gradient profile is intact across the length of the separation path.

In the present invention, some variation in the concentration of the components of the density gradient are possible. The preferred concentration of Percoll is 30% (v/v). A stable density gradient will still form, however, when Percoll is used in the range of 27–33%. Beyond this range, the stability of the density gradient is rapidly diminished and the density profile shows much greater variation over time. In a similar manner, the concentration of sugar is ideally included at 40% (W/W). However a stable gradient will still form if sugar is used between the ranges of 36–44%.

In the art, the most common sugar used in separations is sucrose. However, some protocols for density gradient separation of viral particles indicate that sorbitol results in better preservation of intact viral constituent compounds. In the preferred embodiment, sorbitol is used to separate intracellular organisms. However this invention is adaptable to a wide range of protocols using any of a number of monosachrides or disachrides. These substitutions should not affect the final formation of the density gradients.

In the preferred embodiment, the tube is spun in a Beckman VTi 50 vertical tube rotor. The vertical tube rotor has the advantage of providing a particle pathlength that is only the diameter of the tube. This shortened pathlength allows for efficient separations. However, this invention is adaptable to any of a number of zonal rotors or vertical tube rotors.

The density gradient will form in the present invention once the sugar/Percoll solution is under a centrifugal field. The density profile is dependent on the g-force applied to the gradient material over time. In the present invention, the gradient material will form a density gradient at 242,500×g force or greater. One of ordinary skill in the art would be able to calculate the g-force given the rotor tube radius and the RPMs used in a protocol. This information is also either calculated automatically by most centrifuges or available in the centrifuge rotor manuals.

The following example illustrate the best known method for using the described invention.

EXAMPLE 1
Formation of the Sorbitol/Percoll Mixture 30 g of Percoll is added to 50 g sorbitol. This is stirred over a low heat until the sorbitol has fully dissolved. The final solution is filter sterilized.

EXAMPLE 2

Separation of Intracellular Parasite Particles Using the Sorbitol/Percoll Density Gradient Chlamydia trachomatis, an infectious intracellular parasite, was purchased as a purified, unactivated species. 5.3 ml of the purchased Chlamydia containing particles suspended in PBS (phosphate buffered saline, pH 7.4 including trace amount of ethidium bromide) were added into a 38.5 ml Beckman Quick-Seal tube. The tube was then filled with 33.2 ml of the sorbitol/Percoll mixture made in example 1. The contents of the tube were then thoroughly mixed by agitation and the tube was sealed.

The tube was spun using a Beckman VTi-50 rotor at 5 degrees C. for three hours at 50,000 RPM. Once the spin run has ended, the Chlamydia particles would have isopycnicaly banded at discrete locations along the length of the tube. These bands can then be removed by any tube fractionation method known to those skilled in the art. In this example, the band was removed by inserting a syringe needle through the side of the centrifuge tube into the separated band and slowly withdrawing the plunger of the syringe. The Percoll/sorbitol was removed from the sample by washing the sample with 0.2 M saline solution and recentrifuging the particles under 100,000 force. The buffer can then be decanted and the particles resuspended. The particles can then be analyzed by any of a number of methods known in the art, including PCR to amplify known segments of DNA, Southern blots to probe for known DNA sequences, or Western blots to assay for specific proteins.

We claim:

1. A method of forming a density gradient comprising the steps of:

a. forming a mixture, said mixture comprising 27–33% a colloidal silica sol with nondialysable polyvinyl pyrolidone coating (v/v) and 36–44% sugar (w/w), and b. mixing said mixture until said sugar has fully dissolved, c. transferring said mixture to a centrifuge tube, and d. applying a centrifugal field to said tube until a linear gradient has formed.

2. The method of claim 1 where the amount of a colloidal silica sol with nondialysable polyvinyl pyrolidone coating added is 30% (v/v).

3. The method of claim 1 where the amount of sugar is 40% (w/w).

4. The method of claim 3 where the sugar is sorbitol.

5. The method of claim 3 where the sugar is sucrose.

6. The method of claim 1 in which said centrifugal field is achieved by spinning said tube in a zonal rotor for 3 hours at 242,500×g force at 5 degrees Celsius.

7. The method of claim 1 in which said centrifugal field is achieved by spinning said tube in a vertical tube rotor.

8. A method of forming a density gradient comprising the steps of:

a. forming a mixture, said mixture comprising 27–33% a colloidal silica sol with nondialysable polyvinyl pyrolidone coating (v/v) and 36–44% sugar (w/w), and b. mixing said mixture until said sugar has fully dissolved, and c. centrifuging the mixture using a vertical tube rotor until a linear gradient has formed.

9. The method of claim 8 where the amount of a colloidal silica sol with nondialysable polyvinyl pyrolidone coating added is 30% (v/v).

10. The method of claim 8 where the amount of sugar is 40% (w/w).

11. The method of claim 8 where the sugar is selected from the group consisting of sorbitol and sucrose.

12. A linear density gradient for separation of compounds comprising,

27–33% (v/v) of sterile a colloidal silica sol with nondialysable polyvinyl pyrolidone coating, and 36–44% (w/w) sugar.

13. The linear density gradient of claim 12 where the concentration of a colloidal silica sol with nondialysable polyvinyl pyrolidone coating is 30% (v/v).

14. The linear density gradient of claim 12 where the concentration of sugar is 40% (w/w).

15. The linear density gradient of claim 12 where the sugar is selected from the group consisting of sucrose and sorbitol.

* * * * *